United States Patent [19]

Citri

[11] 4,381,343
[45] Apr. 26, 1983

[54] DETERMINATION OF ANTIBACTERIAL AGENTS

[75] Inventor: Nathan Citri, Jerusalem, Israel

[73] Assignees: Teva Pharmaceutical Industries Ltd., Har Hotsvim; Yissum Research Development Co., Jerusalem, both of Israel

[21] Appl. No.: 248,408

[22] Filed: Mar. 27, 1981

[30] Foreign Application Priority Data

Mar. 27, 1980 [IL] Israel .................................. 59723

[51] Int. Cl.$^3$ .................... C12Q 1/36; C12Q 1/18; C12R 1/085; C12R 1/10
[52] U.S. Cl. ........................................ 435/24; 435/32; 435/834; 435/836
[58] Field of Search ................. 435/24, 32, 34, 36, 435/37, 38, 834, 836

[56] References Cited

U.S. PATENT DOCUMENTS 3,644,177  2/1972  Zyk .
3,941,658  3/1976  Lameris et al. ................... 435/32
4,234,683  11/1980  McMillan ........................... 435/32

OTHER PUBLICATIONS

Gedek, Chemical Abstracts, 88: 4822j, 427 (1978).

*Primary Examiner*—Esther M. Kepplinger
*Attorney, Agent, or Firm*—Browdy & Neimark

[57] ABSTRACT

The presence of $\beta$-lactam antibiotics in test material such as food, infusions, vaccines, blood for transfusion, body fluids, etc. may be determined by:
  seeding a nutrient medium with a $\beta$-lactamase generating bacterium or spores thereof;
  applying a sample of said test material to a site on the so-called nutrient medium;
  then incubating the medium under conditions inducive to the generation of $\beta$-lactamase by said bacteria; and
  assaying the $\beta$-lactamase thus produced.

10 Claims, 4 Drawing Figures

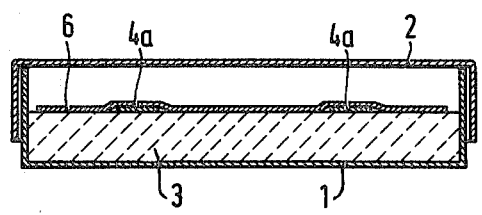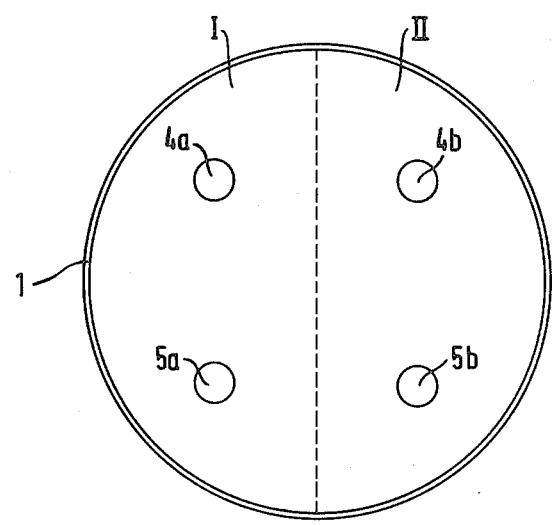

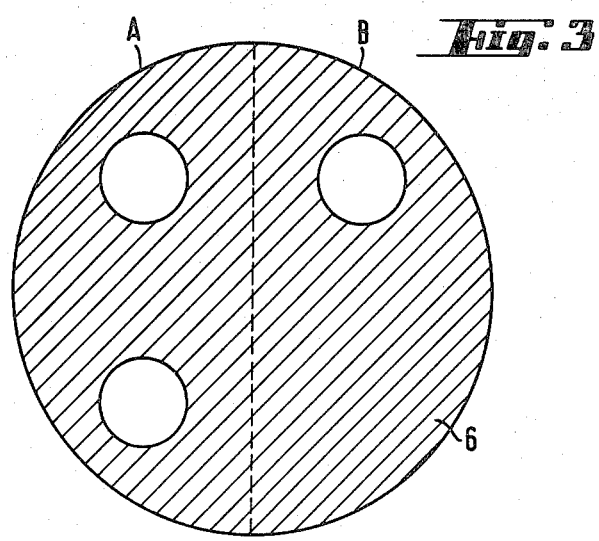
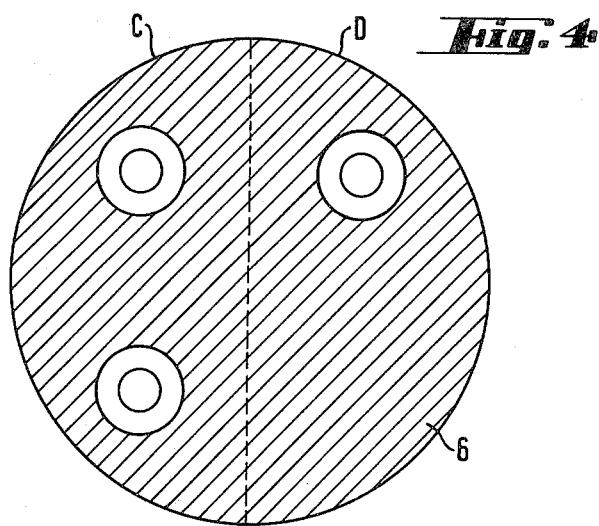

DETERMINATION OF ANTIBACTERIAL AGENTS

The present invention concerns a rapid method for the qualitative detection and semiquantitative measurement of antibiotic substances and other antibacterial agents that are used in human and veterinary medicine, all to be referred to hereinafter as "antibacterial agents". The qualitative detection and semiquantitative measurement of antibacterial agents will be referred to hereinafter indiscriminately as "determination". The fields of applications of the invention are manifold and comprise, inter alia, the determination of antibacterial agents in food, in infusions, in vaccines, in blood for transfusion where it may be necessary, for example, to establish whether a donor's blood contains an antibiotic to which the recipient is sensitive, in body fluids, e.g. blood, to determine the presence and the approximate concentration of an antibacterial agent in the course of antibacterial therapy, etc.

The procedures generally available for the determination of antibacterial agents can be conveniently grouped under the headings of physical, chemical, biochemical, immunological and microbiological. Physical, chemical and immunological procedures require specialized laboratory equipment and services and are not suitable for routine rapid determination.

Known practical methods for the routine rapid determination of antibacterial agents are mostly microbiological. In accordance therewith small amounts of the test material are applied to nutrient broth or nutrient agar plates seeded with bacteria, and after an incubation period the growth of bacteria in the presence of the test material is recorded. When the test material contains an antibacterial agent inhibition of growth will be observed. The parameter of growth most commonly used is increase in the bacterial cell content of the culture. Thus, in broth cultures normal growth causes an increase in turbidity which is not seen in the presence of inhibitory concentrations of an antibacterial agent. Similarly, on plates, turbidity indicates normal growth, whereas a clear zone surrounding the test sample indicates that the sample contains an antibacterial agent. In some tests other parameters associated with growth are used. Thus, the increase in metabolic activity of the growing culture may be assessed with the aid of a color reaction which is specific for a selected metabolic step. In such tests the presence of an antibacterial agent is deduced from the failure of the colour reaction to develop.

The drawback of all the known microbiological methods for the determination of antibacterial agents is the fact that they require several hours of incubation which limits their usefulness. Enormous efforts have been invested by Health Authorities and commercial firms in Europe, the U.S.A. and elsewhere in the attempts to cut down the time required for such tests. The most advanced method is that recently introduced by the Dutch firm Gist-Brocades, the so-called Delvo Test, which under optimal conditions requires an incubation time of $2\frac{1}{2}$ to $2\frac{3}{4}$ hours. This time span, which is still quite long for practical purposes, is as close to the theoretical minimum as one can expect on the basis of the kinetics of bacterial growth.

It is known that enzymes of the group of $\beta$-lactamase are capable of degrading and thereby inactivating $\beta$-lactam antibiotics such as natural and semi-synthetic penicillins and natural and semi-synthetic cephalosporins, and it has already been proposed to make use of this phenomenon for the determination of $\beta$-lactam antibiotics in milk. In accordance with these methods ready-made $\beta$-lactamase enzyme is incubated with a milk sample and thereafter incubated and non-incubated milk samples are assayed microbiologically as described above and comparison of the results obtained with the two samples indicate whether a $\beta$-lactam antibiotic is present or absent. Thus, this test as well is based on the inhibition of bacterial growth and requires a long incubation time as all such tests. Furthermore, it suffers from the additional drawback of being confined to the determination of $\beta$-lactam type antibiotics only.

Since the time required for the determination of antibacterial agents on the basis of the inhibition of bacterial growth is determined by the kinetics of such growth, acceleration beyond the limitations of these kinetics requires a new approach that does not depend on bacterial growth. A biochemical method for the determination of A-type penicillins is disclosed by Naomi Zyk in U.S. Pat. No. 3,644,177. An A-type penicillin is a penicillin that is relatively resistant to penicillinase ($\beta$-lactamase) and in accordance with that method the content of an A-type penicillin is determined in biological, metabolic and alimentary substances by partially inactivating penicillinase with iodine in the presence of a specimen of the test material and measuring the residual activity of the enzyme by contact with a penicillin that is degraded by penicillinase ($\beta$-lactamase) in the presence of an indicator whose color change signifies accumulation of the hydrolyzate penicilloic acid. In addition to being confined to the determination of A-type penicillins only, this method suffers from a relatively low sensitivity which is due to the dissociation constant between the enzyme and the substrate. In consequence a relatively high concentration of the A-type antibiotic in the test material is required or alternatively a long incubation time is needed which, however, defeats the purpose of the method.

It is the object of the present invention to provide an improved method for the determination of antibacterial agents that is fast, reliable, simple to carry out and is capable of determining any antibacterial agent regardless of its chemical nature.

The invention makes use of the known phenomenon that certain strains of bacteria respond to the presence of a $\beta$-lactam antibiotic (hereinafter for short BLA) by producing large amounts of a $\beta$-lactamase. The response is rapid and completely specific in that it is elicited by any BLA but by no other known substance.

The invention provides a method for the determination of a BLA in a test material comprising:

(i) seeding a nutrient medium with $\beta$-lactamase generating bacteria or spores thereof;

(ii) applying a sample of said test material to a site on the so-seeded nutrient medium;

(iii) then incubating the medium under conditions inducive to the generation of $\beta$-lactamase by said bacteria; and (iv) assaying the $\beta$-lactamase thus produced (development).

The invention further provides a method for the simultaneous determination of BLA and non-BLA antibacterial agents in a test material comprising:

(i) seeding a nutrient medium with a strain of $\beta$-lactamase generating bacteria or spores thereof;

(ii) applying to the seeded nutrient medium at two discrete sites two samples of the test material, one of them together with a BLA;
(iii) then incubating the nutrient medium under conditions inducive to the generation of β-lactamase by said bacteria;
(iv) assaying said discrete sites for β-lactamase (development); and
(v) comparing the development of said two sites.

The determination method according to the invention is thus based on the induced generation of β-lactamase by bacteria in the presence only of a BLA. This induction is specific to BLA and the determination according to the invention gives thus answers to the following questions:

(1) Does the test material contain a BLA?
(2) Does the test material contain a significant amount of another, non-BLA antibacterial agent?
(3) Does the test material contain both a BLA and a non-BLA antibacterial agent?

Any suitable chemical or biochemical assay may be used for the development. As a rule color reactions will be preferred.

For the development it is possible to use a BLA that is susceptible to degradation by a β-lactamase, e.g. a penicillin or cephalosporin. Such degradation yields breakdown products, e.g. acids, that can be assayed. For example, if benzylpenicillin (penicillin G) is used, the breakdown product is penicilloic acid which can be assayed, for example, on the basis of its property to liberate iodine from a colorless complex with iodine either free or bound to a carrier molecule such as starch.

The induction of the formation of a β-lactamase by a BLA is a very sensitive and rapid reaction, each BLA molecule giving rise to the formation of a large manifold of the order of 500–1,000 molecules of the enzyme. In consequence, minute quantities of the test material are sufficient for application to the seeded nutrient medium. Accordingly, for the determination of antibacterial agents in accordance with the invention in solid food products, e.g. cheese or meat, a short contact of the test material with the nutrient medium is as a rule sufficient and there is no need to prepare the test material in any way or to produce an extract therefrom.

In accordance with the invention the presence of a BLA and of any other antibacterial agent is indicated separately. The specific detection of contaminant BLA in the presence of other antibacterial agents is particularly important in foodstuffs and many medical supplies (e.g. blood for transfusion, infusion, vaccines, etc.) because of the prevalence of hypersensitivity to penicillins (and cross-reactions with other β-lactams) in the general population. None of the hitherto known and available tests allows determination of both BLA and other non-BLA antibacterial agents in one single operation.

Examples of BLAs that can be determined in accordance with the invention are natural penicillins such as benzylpenicillin (penicillin G), phenoxymethylpenicillin (penicillin V); semi-synthetic penicillins both sensitive and resistant to β-lactamase such as carbenicillin, ampicillin, amoxycillin, oxacillin, cloxacillin, flucoxacillin, methicillin; cephalosporins such as cephalothin, cephaloridine, cephalexin, cafazolin; cephamycins such as cefoxitin.

Examples of non-BLA types of antibacterial agents that can be determined in accordance with the invention are tetracyclines, aminoglycosides, chloramphenicol, sulpha drugs, nitrofurans and many others.

The rate of β-lactamase formation and hence its level at a particular time is generally proportional to the concentration of a β-lactam antibiotic, if any, in the test material within the expected range of contamination of 1.0–1,000 ng/ml. Many sensitive methods for the assay of β-lactamase are known, and it is possible to obtain a nearly quantitative estimate of the BLA in the test sample by comparing its inducing activity with that of a series of controls comprising graded amounts of a reference BLA.

Where the test material contains a mixture of a β-lactam antibiotic and another antibacterial agent the development of the nutrient medium after incubation for indication of the presence of a degradation product of the β-lactam antibiotic will also indicate by way of negative response the presence of said other antibacterial agent. If the nature of the latter is known, quantitative assessment is possible by comparison with the effects produced by mixtures of known relative proportions of the same antibacterial agent and a BLA.

Many bacterial strains are known to produce an inducible β-lactamase in the presence of a β-lactam antibiotic. Examples are *Bacillus cereus* ATCC 10876 also referred to in the literature as Bacillus cereus 569; *Bacillus licheniformis* 749; *Staph. aureus* strains 5974, 13137; *Staph. albus* J-1, J-3; Abraham's strain of *Pseudomonas pyocyanea*. For further examples and particulars reference may be had to Chapter VI, Section D of the review by N. Citri and M. R. Pollock on "The biochemistry and function of β-lactamase" in Adv. Enzylmol., Vol. 28, 237–323 (1966).

Preferred bacteria are *Bacillus cereus* and *Bacillus licheniformis*.

Examples of nutrient media are nutrient-agar plates, filter paper impregnated with nutrient and liquid nutrient media.

The samples of the test material may be applied to the nutrient medium directly. Alternatively, carrier bodies may be used, for example in the form of standard filter paper discs of two kinds, one plain and the other pre-impregnated with a reference β-lactam antibiotic, e.g. a penicillin.

The invention is illustrated, by way of example only, in the accompanying drawings in which:

FIG. 1 is a cross-section through a test arrangement according to the invention;

FIG. 2 is a plan view of a seeded nutrient-agar plate with test samples applied thereto in an arrangement according to FIG. 1, prior to incubation;

FIG. 3 shows the results of a first series of tests; and

FIG. 4 shows the results of a second series of tests.

The testing arrangement illustrated in FIG. 1 comprises a Petri dish 1 containing a nutrient-agar plate 3 and covered with a lid 2. For performance of the test, agar plate 3 is seeded with a strain of bacteria inducible by a β-lactam antibiotic to produce β-lactamase. On discrete sites of the upper face of agar plate 3 are placed sampling discs 4a and 4b. Overlaying plate 3 is a pad 6 impregnated with an aqueous solution of soluble starch and an iodine-iodide mixture, and a phosphate buffer solution of a β-lactam antibiotic, e.g. benzylpenicillin (penicillin G), susceptible to degradation by a β-lactamase. The pad 6 is applied only after an initial incubation period as will now be explained.

FIG. 2 shows the arrangement of applied samples of two tests I and II, prior to incubation. As shown, each test comprises a pair of sampling discs, 4a, 5a for test I and 4b, 5b for test II. Of these discs 4a and 4b are pre-impregnated with a β-lactam type antibiotic, e.g. benzylpenicillin. In addition all four discs are impregnated with test material which is the same for the pair of discs 4a, 5a and again the same for discs 4b, 5b. The samples for tests I and II are of different origin.

After impregnation of the sampling discs the covered Petri dish, as yet without the pad 6, is incubated for 40 to 50 minutes at 37° C. After this incubation period the pad 6 is overlaid on plate 1 and the discs as shown in FIG. 1. After overlying of the pad 6, lid 2 is restored and the assembly is incubated for another 5–10 minutes. During this second incubation period any β-lactamase generated during the first incubation period degrades the penicillin in pad 6 at the sites overlaying the discs insofar as the samples of test material thereon contained a BLA. This always holds true for discs 4a and 4b which had been impregnated with a BLA before the addition of the test material, and may or may not be true for either of discs 5a and 5b. Any penicilloic acid that forms on said sites binds and decolorizes the iodine with the result that the initially blue-black color of the starch-iodine complex disappears. In consequence white zones are formed on pad 6 at the sites overlaying discs 4a and 4b and may also form at the sites overlaying discs 5a and 5b insofar as a β-lactam antibiotic was present in the test material.

The presence of a mixture of a β-lactam antibiotic and another non-BLA antibacterial agent shows up as a dark center within the white zone. The induction is specific to BLA and is inhibited in close proximity to the disc where the non-BLA antibacterial agent is most concentrated. The diameter of the dark center is roughly proportional to the amount of said non-BLA antibacterial agent. Complete inhibition of induction, i.e. no white zone, will occur with very large excess of the non-BLA antibacterial agent.

The invention is further illustrated in the following Examples without being limited thereto.

EXAMPLE 1

Test for antibiotics in milk

A test arrangement as described hereinbefore with reference to FIGS. 1 and 2 was used. The nutrient-agar plate 3 was seeded with *Bacillus cereus* ATCC 10876, deposited prior to the filing of this application at the American Type Culture Collection, 12301 Park Lane Drive, Rockville, Mc. Discs 4a and 4b were impregnated with benzylpenicillin. The diameter of these discs and of the plain discs 5a, 5b was 4 mm.

For the preparation of a pad 6 a filter paper pad of 85 mm diameter was impregnated with an aqueous solution containing 25 mM of iodine, 125 mM of potassium iodide and 2% by weight of soluble starch. After this impregnation the pad was air dried and stored with desiccant in an air-tight dark container. The pairs of discs 4a, 5a and 4b, 5b were used for testing different milk samples. On each of plates 4a and 5a a drop of a first milk sample was placed and on each of discs 4b and 5b a drop of a second sample. Lid 2 was restored and the assembly was incubated for 40 minutes at 37° C. In the meantime 100,000 units of benzylpenicillin were dissolved in 5 ml of 0.1 M phosphate buffer of pH 6.8. Pad 6 was soaked in this solution and at the end of the first incubation period was overlaid on the agar plate 1. The lid was replaced and the assembly was incubated for another 5–10 minutes.

In FIGS. 3 and 4 the test results with 4 milk samples A, B, C and D are diagrammatically illustrated and these results are tabulated and interpreted in the following Table I.

TABLE I

| Milk sample | Penicillin disc White Zone | Penicillin disc Dark Center | Plain disc White Zone | Plain disc Dark Center | Contaminant |
|---|---|---|---|---|---|
| A | + | − | + | − | BLA (β-lactam antibiotic) |
| B | + | − | − | − | No contaminant |
| C | + | + | + | + | Mixed (β-lactam + other antibacterial agent(s)) |
| D | + | + | − | − | Antibacterial agent(s) other than BLA |

It is seen from the foregoing Example that BLA and non-BLA antibacterial agents were determined simultaneously in one test which lasted about 45–60 minutes, i.e. about ⅓ of the duration of the hitherto fastest known microbiological test.

EXAMPLE 2

Screening of blood for transfusion

Routine screening of blood-bank stock by conventional growth inhibition test revealed that 7 donor blood samples had antibiotic activity which was not eliminated by incubation with penicillinase. It was therefore important to determine specifically whether any of these samples contained β-lactam antibiotics which are resistant to penicillinase. No hitherto available screening test can distinguish between β-lactams and other antibiotics that are not of the β-lactam series.

The problem was resolved by testing in accordance with the invention. The test arrangement was similar as in Example 1 and FIGS. 1 and 2. However, in this case the sampling discs were omitted and 0.05 ml of each blood was placed on a marked spot on a seeded plate. The plates were incubated and developed as in Example 1 and the results are shown in the following Table II.

TABLE II

| Blood Sample | White zone | Dark Center | Conclusions |
|---|---|---|---|
| 1 | − | − | No BLA |
| 2 | + | + | BLA and non-BLA present |
| 3 | − | − | No BLA |
| 4 | − | − | No BLA |
| 5 | + | − | BLA alone present |
| 6 | + | − | BLA alone present |
| 7 | + | − | BLA alone present |

A semi-quantitative estimate of the level of any known non-BLA antibiotic can be obtained by the following procedure. A reference chart is constructed based on the effect of mixtures of graded amounts of that antibiotic with 0.1 μg/ml of a BLA, e.g. benzylpenicillin. The sample containing the unknown amount of that antibiotic is then supplemented with 0.1 μg/ml of the BLA and applied to the seeded plate as in Example 2. The results are interpreted with the aid of the reference chart.

If desired, the induction test may be performed in liquid media rather than on plates and the induced β-lactamase may be detected with the aid of agents in solution rather than impregnated pads.

The starch in the starch-iodine complex may be replaced with other chromogenic complexants such as, for example, polyvinyl alcohol. Such complexants may be incorporated in the seeded medium if they are not inhibitory in themselves.

The time and temperature of the incubation may be varied as convenient within fairly wide limits. Thus, when incubation facilities are unavailable and the time factor is not crucial, induction and development may be carried out at ambient temperatures. For example, at about 20° the test will require about 2 hours. Conversely, it is possible to shorten the time of the test significantly by carrying out the incubation at higher temperatures. The optimal temperature for *Bacillus cereus* strain 569 is 43° C., but it is easy to select mutants of this and other inducible β-lactamase producers which will thrive at higher temperatures or, alternatively, to derive inducible β-lactamase producers from known thermophilic bacterial species. The use of such strains will allow further reduction in the time required for both induction and development.

Detection of β-lactamase induction need not be based on iodine uptake by the acid formed. Any other simple and sensitive method will serve the purpose. Thus, for instance, an acidic breakdown product will reduce the pH of the medium and cause change of color in a suitable pH indicator. The indicator may be incorporated in the nutrient medium or applied in a pad or in the substrate solution which may be sprayed on the nutrient medium.

EXAMPLE 3

Monitoring gentamicin in circulation

The reagents and the material are the following:
(1) A logarithmic phase of culture of *Bacillus licheniformis* strain 749.
(2) Starch-iodine strips 3 mm×3 mm cut from pads prepared as in Example 1.
(3) Benzylpenicillin solution and penicillin discs as in Example 1.
(4) A disposable microtiter plate.
(5) A reference chart for the gentamicin test.

A penicillin disc is wetted with water and touched with a swab. The swab is then used for wiping a well in a nutrient-agar plate. The so-prepared well contains enough penicillin for maximal induction ("penicillin well"). A required number of penicillin wells is prepared in this way.

Blood samples of 50 μl each are obtained from finger tips of patients who had been treated with gentamicin. Each of the blood samples is placed in a penicillin well together with 50 μl of the bacterial culture, and the test assembly is incubated at 37° C. for a first incubation period of 35 minutes.

A starch-iodine strip is dipped in the benzylpenicillin solution and is then, at the end of the first incubation period, placed in the blood culture. Incubation is continued for a second incubation period of 10 minutes.

The time required for complete decolorization of each strip is recorded.

The time required for decolorization of the strip is directly proportional to the level of gentamicin in the cirulation. A semiquantitative estimate can be obtained from the chart. If the strip is not decolorized within 10 minutes it may be concluded that gentamicin is present in excess. This should be confirmed by control blood samples known to contain no gentamicin and a known amount of gentamicin respectively.

I claim:
1. A method for the simultaneous determination of a β-lactam antibiotic (BLA) and a non-BLA antibacterial agent in a test material, comprising:
   (i) seeding a nutrient medium with a strain of β-lactamase generating bacterium or spores thereof;
   (ii) applying to the seeded nutrient medium at two discrete sites two samples of the test material, one of them together with a BLA;
   (iii) then incubating the nutrient medium under conditions inducive to the generation of β-lactamase by said bacteria;
   (iv) assaying said discrete sites for β-lactamase (development); and
   (v) comparing the development of said two sites.
2. A method according to claim 1, wherein said bacterium is *Bacillus cereus*.
3. A method according to claim 1, wherein said bacterium is *Bacillus licheniformis*.
4. A method according to claim 1, wherein a penicillin or cephalosporin susceptible to degradation by β-lactamase is used for the development and the resulting breakdown product is assayed.
5. A method according to claim 4, wherein the breakdown product is penicilloic acid and iodinated polysaccharide is used for the assay.
6. A method according to claim 4, wherein the breakdown product is an acid and a pH indicator is used for the assay.
7. A method according to claim 1, wherein the concentration of BLA in the sample of test material is estimated by comparing the results of development with a chart based on the results with a series of controls comprising graded amounts of a reference BLA.
8. A method according to claim 1, wherein the concentration of the non-BLA antibacterial agent in the test sample is estimated by supplementing said sample prior to testing with a given amount of a BLA and comparing the results of development with a chart based on the results obtained with mixture containing the same amount of the same BLA and graded amounts of said non-BLA antibacterial agent.
9. A method according to claim 1, wherein the samples of test material are applied directly to said nutrient medium.
10. A method according to claim 1, wherein the samples of test material are placed on sampling discs which are applied to said nutrient medium.

* * * * *